Figure 1:
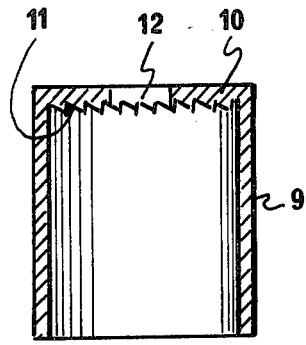
Figure 1:
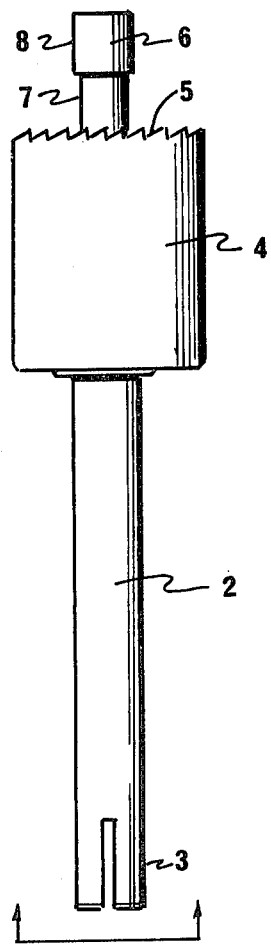

United States Patent [19]

H:son Olde

[11] Patent Number: 4,465,463
[45] Date of Patent: Aug. 14, 1984

[54] DRIVING TOOL

[76] Inventor: Rune H:son Olde, Klintvägen 58, S-752 46 Uppsala, Sweden

[21] Appl. No.: 492,331

[22] Filed: May 6, 1983

[30] Foreign Application Priority Data

May 10, 1982 [SE] Sweden ................................ 8202927

[51] Int. Cl.³ .............................................. A61C 3/00
[52] U.S. Cl. ..................................... 433/141; 433/225
[58] Field of Search ....................... 433/225, 141, 126; 81/121, 225

[56] References Cited

U.S. PATENT DOCUMENTS 1,201,562 10/1916 Cooper ............................ 81/121 R
2,103,944 12/1937 Gullborg .......................... 81/121 R
4,142,293 3/1979 Tieche .................................. 433/225

FOREIGN PATENT DOCUMENTS 905714 12/1968 Canada ................................ 433/225

Primary Examiner—Robert Peshock
Attorney, Agent, or Firm—Witherspoon & Hargest

[57] ABSTRACT

The present invention relates shortly to a driving tool for screwing rods into teeth. This tool includes a stem (2) having an attachment means (3) for a rod in one end thereof and an operating portion (4, 9) in the other end thereof. The operating portion includes a removable sleeve (9) which surrounds the operating portion end (4) of the stem (2) and which is limitedly movable in the longitudinal direction of the stem (2). The operating portion end is preferably constituted by a cylindrical head (4) having circular cross-section and slightly greater diameter than the stem. On the operating portion end or the head (4) there are engagement means (5) and within the sleeve (9) there are cooperating engagement means (11) which engagement means (5, 11) are brought into and out of engagement respectively by the movement of the sleeve (9) between its limiting positions.

5 Claims, 3 Drawing Figures

U.S. Patent   Aug. 14, 1984   4,465,463

DRIVING TOOL

The present invention relates to driving tools and more precisely to a driving tool for screwing rods into teeth.

In connection with such mending of teeth which involves attachment of a crown or a bigger piece of filling material such as amalgam on a remaining portion of a tooth there is very often used a rod which is fastened as a screw in the tooth and the raising portions constitute an attachment for the filling or the crown. These rods are provided with a cylindrical or slightly conical threaded stem which is screwed down into a hole bored in the tooth and having a diameter adapted to the actual rod.

Such rods are usually of a diameter of about 1 mm and due to the small size of the rods there is, accordingly, required a special tool for the screwing or driving operation. A tool which is very often used includes a stem having a diameter of between 2 and 3 mm and a length of between 6 and 10 mm. The end of the stem intended for receiving and holding the rod during screwing operations is shaped as a simple jaw comprising a hole extending inwards from the end of the stem and having a sectional shape corresponding to the one of the holding end of the rod, usually square shape, and a diametrical slit through the stem extended through two opposite corners of the square. At the other end of the stem there is a cylindrical head constituting the operating portion of the tool. Said head is not allowed to be too big as in such a case it would be too easy to transfer so great forces to the rod that the rod or the tooth is drawn into pieces. Preferably, the diameter of the operating head is between 6 and 10 mm.

As is clear from what is stated above the tool is intended to be used for a work which is very similar to fine mechanics and as it is so small it is some times difficult to get a satisfactory grip on the tool. Accordingly, there is a risk that the dentist might loose the grip on the small tool especially as he or she at short intervals has to relieve the grip on the operating head in order to take a new grip for the continued turning for driving the rod. If the dentist should loose the tool it can easily happen that the tool is slipping down into the throat of the patient and also down into the tracheas as the treatment of the patient nowadays mostly takes place having the patient in a lying position. If the tool should move down into the tracheas it can be removed only by a surgical incision.

The object of the present invention is to bring about a driving tool of the type mentioned in connection with which the risk for the dentist to loose the tool has been essentially reduced. This object is reached by a driving tool of the type referred to in the claims from which also the features especially characterizing the invention are clear.

Figure 2:
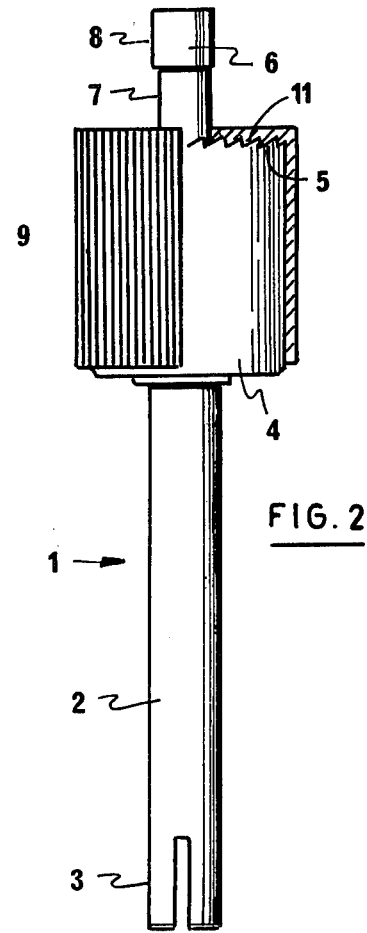
Figure 3:
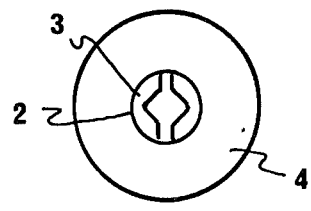

The invention is closer described in the following in connection with the attached drawing in which FIG. 1 shows one embodiment of the tool in accordance with the invention in a disassembled relation and partially in section, FIG. 2 shows the tool in FIG. 1 in assembled condition and partially in section, and FIG. 3 is a view from the end of the tool at which the rod is hold.

The tool 1 in accordance with the invention comprises in the shown embodiment a stem 2 which at one end has a jaw-like attachment 3 and which at the other end has a cylindrical enlargement or a cylindrical head 4 of circular cross-section. The head 4 is at the side faced from the stem 2 provided with engagement means 5 in the shape of radially extended and axially protruding ridges of a saw-tooth like sectional shape. A pin 6 is extending centrally outwards from the side of the head 4 provided with the engagment means 5. The pin 6 has an inner portion 7 and an outer portion 8, the outer portion 8 being of slightly greater diameter than the inner portion 7.

A tubular sleeve 9 is intended to be threaded over the head 4 and it can be axially moved and turned around the head 4. The sleeve 9 has an end wall 10 on the side of which being faced inwards there are engagement means 11 which are complementary to the engagement means 5 on the head 4. Through the end wall 10 there is also a central opening 12 having a diameter which is such that the sleeve 9 when mounted over the head 4 has to be forced over the outer portion 8 of the pin 6 but then being able to run freely around and along the inner portion 7 of the pin 6.

In FIG. 2 the tubular sleeve 9 is shown mounted on the head 4 and having the engagement means 5 and 11 in engagement. The inner portion 7 of the pin 6 is slightly longer than the height of the engagement means 5, 11 so that the sleeve 9 can be axially moved between the shown engagement position and a position in which the engagement means 5, 11 are out of engagement while portion 8 of the pin 6 prevents the sleeve 9 from getting loose.

In an alternative embodiment of the invention the pin 6 is substituted by a screw the head of which is resting against the outer side of the end wall 10 when the sleeve 9 is in position to be turned freely around the head 4.

From FIG. 3 there is clear an embodiment of the jaw-like attachment 3. However, it is self-evident that said attachment 3 can be of some other shape depending upon the shape of the portion of the rod together with which this attachment has to cooperate.

The stem 2 is normally of a diameter between 2 and 2.5 mm and the head 4 between 5 and 6 mm and the sleeve 9 between 7 and 8 mm. It is here concern of a very small tool which has to be possible to clean and sterilize without problems. Indeed, it should be possible to make use of some other shape of latching mechanism but such a mechanism should easily be destroyed when actuated by saliva and particles emanating from the tooth repair and further, it should be very difficult to disassemble for cleaning and sterilizing. In the structure in accordance with the present invention, there are no small parts which may be damaged and the sleeve can easily be separated from the rest of the tool for cleaning and sterilizing without being damaged in connection therewith. Due to the simple structure the tool is also cheap both to manufacture and to assemble.

The driving tool in accordance with the invention is used in the following way:

Having chosen a suitable rod and bored a receiving hole for the rod in the tooth the rod is attached in the jaw-like attachment 3 so that the threaded portion of the rod constitutes an elongation of the stem 2. Thereafter, the dentist grips around the sleeve 9 with the thumb and the forefinger and guides the rod to the entrance of the receiving bore. In this position the dentist presses carefully the rod down into the bore simultaneously as he is rolling the sleeve 9 clockwise between the fingers. When the dentist has rolled the sleeve 9 as long as allowed by the fingers he or she has to take a new grip, and in contrast to prior tools in connection with which it was necessary completely to remove the grip on the tool, this takes now easily place by the fact that the dentist draws the sleeve 9 outwards the distance allowed by the portion 7 of the pin 6 or by the retaining screw not shown, rolls the sleeve 9 backwards counter-clock-wise between the fingers in order thereafter to move the sleeve 9 downwards towards the head 4 so that the engagement between the engagement means 5, 11 once again is restored and the driving can be repeated.

One realizes that the driving tool in accordance with the present invention is essentially more safe to use than prior corresponding tools due to the fact that the dentist never needs to loosen the grip on the tool during the whole driving operation. There are neither any cleaning problems as the sleeve 9 may be removed by a simple measure and then does not show any complicated details which might make the cleaning and sterilizing difficult.

As an extra safety precaution the pin 6 may be provided with a through-bore in the outer portion 8 in which a thread is secured which then may be hanging out through the mouth of the patient so that if the dentist in spite of everything should loose the tool this can easily by drawn back by the aid of said thread.

I claim:

1. A tool for screwing a rod into a tooth comprising a stem, one end of which includes means for operatively engaging said rod and the other end of which includes an enlarged cylindrical head, the end of said head furthest from said engaging means including a first plurality of saw-tooth-like ridges;
a cylindrical sleeve one end of which is open and the other end of which is closed, the surface of said closed end internal of said sleeve including a second plurality of saw-tooth-like ridges and said closed end including an aperture through the center thereof, said enlarged cylindrical head being positioned within said cylindrical sleeve such that said first and second plurality of ridges are adjacent one another; and,
a pin axially extending from said end of said head through said aperture, the end of said pin outside of said sleeve including means to maintain said head within said sleeve and to allow said sleeve to freely reciprocate axially relative to said pin to engage said first and second plurality of ridges when desired such that rotation of said sleeve rotates said head and said engaging means, and to disengage said first and second plurality of ridges when desired such that said sleeve may be freely rotated about said pin.

2. The tool of claim 1 wherein said maintaining means includes an enlarged end portion of said pin, the width of said pin being greater than the width of said aperture to require that said enlarged end be force fitted through said aperture.

3. The tool of claim 2 wherein said pin is a screw.

4. The tool of claim 2 wherein said first and second plurality of ridges comprise a plurality of radially extended and axially protruding ridges.

5. The tool of claim 2 wherein said pin, said stem and said enlarged end portion are cylindrical members and said aperture is circular.

* * * * *